United States Patent [19]
Hashino et al.

[11] Patent Number: 5,648,078
[45] Date of Patent: Jul. 15, 1997

[54] METHOD FOR INHIBITING METASTASIS OF COLON CANCER TO THE LIVER

[75] Inventors: Junko Hashino; Shinzo Oikawa, both of Kyoto; Hiroshi Nakazato; Toshihiro Nakanishi, both of Ibaraki, all of Japan

[73] Assignee: Suntory Limited, Osaka, Japan

[21] Appl. No.: 129,195

[22] PCT Filed: Feb. 12, 1993

[86] PCT No.: PCT/JP93/00182

§ 371 Date: May 11, 1994

§ 102(e) Date: May 11, 1994

[87] PCT Pub. No.: WO93/16128

PCT Pub. Date: Aug. 19, 1993

[30] Foreign Application Priority Data

Feb. 14, 1992 [JP] Japan ......................................... 4-59551

[51] Int. Cl.$^6$ ..................... A61K 39/395; C07K 16/18; C07K 16/28; C07K 16/30
[52] U.S. Cl. ...................... 424/156.1; 424/155.1; 424/174.1; 530/388.85; 530/388.8
[58] Field of Search ........................ 530/388.8, 388.85; 424/174.1, 155.1, 156.1

[56] References Cited

U.S. PATENT DOCUMENTS 4,348,376 9/1982 Goldenberg ......................... 424/1

FOREIGN PATENT DOCUMENTS

| | | |
|---|---|---|
| 0323805 | 7/1989 | European Pat. Off. |
| 59-5120 | 1/1984 | Japan |
| 63-177794 | 7/1988 | Japan |
| 5-119037 | 5/1993 | Japan |
| 9201059 | 1/1992 | WIPO |

OTHER PUBLICATIONS

American Journal of Clinical Pathology, vol. 94, No. 2, pp. 157–164, Aug. 1990, K. Sheahan, et al., "Differential Reactivities Of Carcinoembryonic Antigen (CEA) CEA-Related Monoclonal and Polyclonal Antibodies In common Epithelial Malignancies".
Journal of Surgical Oncology, vol. 42, No. 1, pp. 39–46, Sep. 1989, Y. Sakurai, et al., "Conformational Epitopes Specific To Carcinoembryonic Antigen Defined By Monoclonal Antibodies Raised Against Colon Cancer Xenografts".
Cancer Research, vol. 49, No. 17, pp. 4852–4858, Sep. 1, 1989, S. Hammarstrom, et al., "Antigenic Sites In Carcinoembryonic Antigen".
Primus, F. J. et al., Cancer Research, 43:686–692, Feb. 1983.
Sutherland, R. et al., Cancer Research, 47(6):1627–1633, 1987.
Hashino, J. et al., Biochem & Biophys Res. Commun, 197(2):886–893, Dec. 15, 1993.
Blakeslee, S., The Globe & Male, Section B, p. 4, Jul. 8, 1989.
Waldmann, T., Science, 252:1657–1662, 21 Jun. 1991.
Kuroki, Masahide et al., Immunological Investigations, 21(2), 143–158, Feb. 1992.
Tsujisaki, M. et al., Int. J. Cancer, 47:267–273, 1991.
Begent, R.H.J., Genes and Cancer, edited by D. Carney J K. Sibora, 1990, pp. 173–182.
"Specific adhesion of carcinoembryonic antigen–bearing colorectal cancer cells to immobilized carcinoembryonic antigen." Larissa V. Levin and Thomas W. Griffin, Cancer Letters, 60(2), 1991, pp. 143–152.
"Primary Structure of Human Carcinoembryonic Antigen (CEA) deduced from cDNA Sequence." Oikawa, et al. Biochemical and Biophysical Research Communications, vol. 142, No. 2, Jan. 30, 1987, pp. 511–518.
"Preparation of Monoclonal Antibodies to Synthetic Peptide of Carcinoembryonic Antigen (CEA) and Analysis of Epitopes on CEA." Hishikawa et al., Sapporo Medical Journal, vol. 58, No. 5, 1989, pp. 295–305.
Proceedings of the American Association for Cancer Research, Mar. 1992, vol. 33, Levin, et al., p. 207.
Proceedings of the Japanese Cancer Association, 51st Annual Meeting, J. Hashino, et al., Sep. 1992, Osaka, p. 199, (with English translation).
Molecular Immunology, vol. 29, No. 2, pp. 229–240, 1992, Shoichi Ikeda, et al., "Epitope Mapping Of The Carcinoembryonic Antigen With Various Related Recombinant Proteins Expressed In Chinese Hamster Ovary Cells And 25 Distinct Monoclonal Antibodies".
Cancer Research, vol. 44, pp. 3522–3529, Aug. 1984, James M. Kozlowski, et al., "Metastatic Behavior Of Human Tumor Cell Lines Grown In The Nude Mouse".
Nature, vol. 256, Aug. 7, 1975, G. Kohler, et al., "Continuous Cultures Of Fused Cells Secreting Antibody Of Predefined Specificity".
Cell, vol. 57, pp. 327–334, Apr. 21, 1989, Sarita Benchimol, et al., "Carcinoembryonic Antigen, A Human Tumor Marker, Functions As An Intercellular Adhesion Molecule".
Biochemical and Biophysical Research Communications, vol. 164, No. 1, 1989, Oct. 16, 1989, pp. 39–45, Shinzo Oikawa, et al., "Cell Adhesion Activity Of Non–Specific Cross–Reacting Antigen (NCA) And Carcinoembryonic Antigen (CEA) Expressed On Cho Cell Surface: Homophilic And Heterophilic Adhesion".
The Journal of Biological Chemistry, vol. 263, No. 25, Sep. 5, 1988, Noboru Takami, et al., pp. 12716–12720, "Evidence For Carboxyl–Terminal Processing And Glycolipid–Anchoring Of Human Carcinoembryonic Antigen".

(List continued on next page.)

Primary Examiner—Susan A. Loring
Attorney, Agent, or Firm—Oblon, Spivak, McClelland, Maier & Neustadt, P.C.

[57] ABSTRACT

The metastasis of cells, which express a glycoprotein of human carcinoembryonic antigen on the cells surfaces, is inhibited in a living organ by administering, in advance, to a subject, a monoclonal antibody which binds a peptide which comprises at least the peptide sequence of domain N in the glycoprotein of human carcinoembryonic antigen.

4 Claims, 2 Drawing Sheets

OTHER PUBLICATIONS

Proc. Natl. Acad. Sci. USA, vol. 85, pp. 4648–4652, Jul. 1988, Biochemistry, Stanley A. Hefta, et al., "Carcinoembryonic Antigen Is Anchored To Membranes By Covalent Attachment To A Glycosylphosphatidylinositol Moiety: Identification Of The Ethanolamine Linkage Site".

Biochemical and Biophysical Research Communications, vol. 150, No. 1, 1988, Jan. 15, 1988, pp. 89–96, Yasunori Tawaragi, et al., "Primary Structure Of Nonspecific Cross reacting Antigen (NCA), A Member Of Carcinoembryonic Antigen (CEA) Gene Family, deduced From cDNA Sequence".

Biochemical and Biophysical Research Communications, vol. 142, No. 2, 1987, Jan. 30, 1987, pp. 511–518, Shinzo Oikawa, et al., "Primary Structure Of Human Carcinoembryonic Antigen (CEA) Deduced From cDNA Sequence".

Cancer and Metastasis Reviews, vol. 8, pp. 263–280, 1989, J. Milburn Jessup, et al., "Carcinoembryonic Antigen: Function In Metastasis By Human Colorectal Carcinoma".

METHOD FOR INHIBITING METASTASIS OF COLON CANCER TO THE LIVER

TECHNICAL FIELD

This invention relates to a monoclonal antibody against a peptide which imparts adhesion activity to human cancer cells when expressed on cell surfaces and also to a cell adhesion inhibitor making use of the monoclonal antibody.

BACKGROUND ART

Carcinoembryonic antigen (hereinafter abbreviated as "CEA") is a glycoprotein discovered in 1965 by Gold and Freedman as an antigen which is found in both human colon cancer and the digestive organs of a 2–6 months old human embryo and having a molecular weight of 180,000 to 200,000 [Gold, P. & Freedman, S. O., J. Exp. Med., 121, 439 (1965)]. Its usefulness in cancer clinic has been widely recognized. It is a tumor marker which is used most often these days.

Further, it became evident by subsequent research that substances similar to CEA, that is, CEA-related antigen also exists in normal human tissues.

The term "CEA-related antigen" is a generic term for a group of antigens which are extremely similar to CEA in both proteinchemistry and immunology. Known typical CEA-related antigens include a nonspecific cross-reactive antigen which is a glycoprotein found in the lungs and spleen of a normal human being and having a molecular weight of about 90,000 [hereinafter abbreviated as "NC"; von Kleist, S. et al., Proc. Natl. Acad. Sci. U.S.A., 69, 2492 (1972)], NCA-2 found in embryonic feces [Burtin, P. et al., J. Immunol., 111, 1926 (1973)], and NFA (normal fecal antigen) found in normal adult feces [Kuroki, M. et al., Cancer Res. 41, 713 (1981)].

They are however still unknown in many aspects, including their detailed molecular structures and their differences in molecular structure.

Keeping step with changes in the diets of Japanese in recent years, colon cancer patients are increasing. About 80% of colon cancer is said to metastasize to the liver, and colon cancer is also said to metastasize to other organs such as the lungs. Recently, there has also been reported the possibility that the cell adhesion activity of CEA may take part in the metastasis of colon cancer to the liver [Jessup, J. M. et al., Cancer and Metastasis Reviews, 8, 263 (1989)].

Using a molecular biological technique, the primary structure of peptide has recently been ascertained with respect to CEA [Oikawa, S. et al., B.B.R.C., 142, 511 (1987) and Japanese Patent Laid-Open No. 177794/1988], NCA [Tawaragi, Y. et al., B.B.R.C., 150, 89 (1988)], BGPI [Hinoda, Y. et al., Proc. Natl. Acad. Sci. U.S.A., 85, 6959 (1988)] and W272 (CGM6) [Arakawa, F. et al., B.B.R.C., 166, 1063 (1990)].

According to the results of a cDNA analysis, CEA peptide is composed of 668 amino acids as shown, for example, in FIG. 3 of Japanese Patent Laid-Open No. 177794/1988.

As is evident from the figure, CEA peptide can be divided into five domains, that is, domain N (1–108) extending from the N terminal to the 108th amino acid, domain I (109–286), domain II (287–464) and domain III (465–642) having mutually very homogeneous repetitive structures and composed individually of 178 amino acids, and domain M (643–668) composed of twenty-six, primarily hydrophobic amino acids on the side of the C terminal. Domains I, II and III may each be divided further into sub-domains (which may also be called "domains") which consist of 92 amino acid residues and 86 amino acid residues, respectively.

These individual sub-domains may also be referred to as "1A", "1B", "2A", "2B", "3A" and "3B", respectively.

These individual domains and CEA peptide constructed of them are schematically illustrated at the top in FIG. 1 of Japanese Patent Application No. 222379/1991.

Domain M was first considered to be anchored on a cell membrane. It is however known that, after translation, domain M is processed and PI-G (phosphatidylinositol glycan) is added instead and is anchored on a cell membrane [Hefta, S. A. et al., Proc. Natl. Acad. Sci. U.S.A., 85, 4648 (1988); Takami N. et al., J. Biol. Chem., 263, 12716 (1988)].

All 12 cysteine residues are found in domains I, II and III, each domain having 4 residues at the same positions as others. Two loops are formed, one being located between the first cysteine and the second cysteine and consisting of 47 amino acids and the other between the third cysteine and the fourth cysteine and 39 amino acids, whereby CEA is considered, as a whole, to have a shape in which six loops are held.

NCA, on the other hand, contains domain N consisting of 108 amino acids and domain I consisting of 178 amino acids. Portions corresponding to domains II and III of CEA are however not found and, in continuation with domain I, there is domain M composed of 24 amino acids which are primarily hydrophobic. The structure of domain I of NCA shows homology slightly lower than 90% to that of CEA in terms of amino acids and the positions of the four cysteine residues contained therein are exactly the same. BGPI is a CEA-related antigen which is found in bile [Svenberg, T. et al., Int. J. Cancer, 17, 588 (1976)]. By a cDNA analysis, BGPI has been found to contain domain A', transmembrane domain and a cytoplasmic domain, which are characteristic to BGPI, after domain N and domain I.

W272 is a CEA-related antigen isolated from human leukocytes (granulocytes) and has a domain structure similar to NCA.

Biological activities of the CEA family have long remained unknown but, recently, CEA and NCA have been found to have cell adhesion activity [Oikawa, S. et al., B.B.R.C., 164, 39 (1989); Benchimol, S. et al., Cell, 57, 327 (1989)]. Namely, it has been found that cells with both CEA and NCA expressed on their surfaces firmly adhere to each other and also that cells with CEA expressed thereon and those with NCA expressed thereon strongly adhere to each other.

However, it has not been ascertained in which regions of CEA and NCA cell adhesion activity is present. This has remained as a bottleneck for the efficient production of a monoclonal anti-CEA antibody which inhibits the cell adhesion activity of CEA.

Any monoclonal antibody against the whole CEA molecule unavoidably contains many antibodies which in turn recognize peptides as epitopes other than the region (domain) having the cell adhesion activity of CEA. To permit efficient production of a monoclonal antibody capable of inhibiting the cell adhesion activity of CEA, it has been necessary to identify the region having the cell adhesion activity of CEA and also to determine its minimum peptide unit.

DISCLOSURE OF THE INVENTION

The present inventors found that determination of a portion on the molecule of CEA, said portion being involved in cell adhesion, makes it possible to synthesize a peptide corresponding to the amino acid sequence of the region and hence to obtain an antibody capable of inhibiting cell adhesion or, by using *Escherichia coli* or animal cells in a manner known per se in the art, to produce in a large quantity an antibody capable of inhibiting cell adhesion.

It was also found that an anti-CEA cell adhesion monoclonal antibody produced using the above peptide can be used, for example, as an active ingredient of a cell adhesion inhibitor such as cancer metastasis inhibitor.

Based on these findings, the present inventors have conducted extensive research according to a molecular biological technique with a view toward identifying the adhesion domain by establishing cell lines, which express a deletion antigen of CEA, a chimeric antigen with NCA, and BGPI and W272, both CEA-related antigens, respectively, and checking the cell adhesion activities of various combinations.

As a result, it has hence been found that a peptide, which contains at least the peptide sequence of domain N and the peptide sequence of a part or the entire part of domain III in the glycoprotein of the human CEA or sequences homologous to these peptide sequences, is involved in cell adhesion activity and use of the peptide as an antigen enables one to obtain an antibody with inhibitory activity of cell adhesion, leading to the completion of the present invention.

The term "peptide sequence having homology" as used herein means a sequence which includes substitution, deletion, addition or the like of one or more amino acids in a part of the sequence, is not identical to the original peptide sequence but is mostly the same as the original peptide sequence and, moreover, has substantially the same function as the original peptide.

BEST MODE FOR CARRYING OUT THE INVENTION

Figure 1:
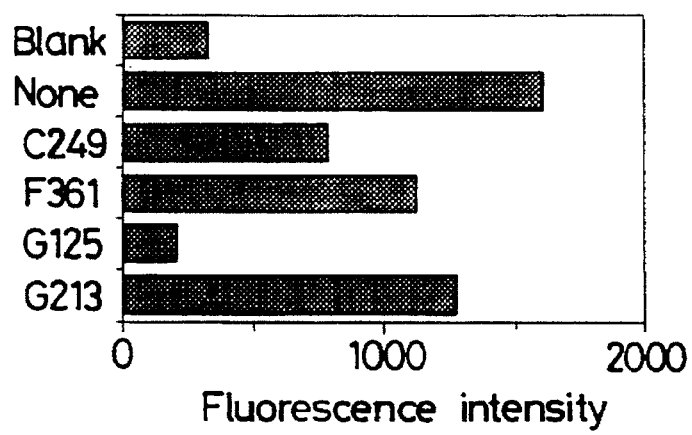
FIG. 1 diagrammatically illustrates adhesion activities of monoclonal antibodies of the present invention against CEA.
Figure 1:
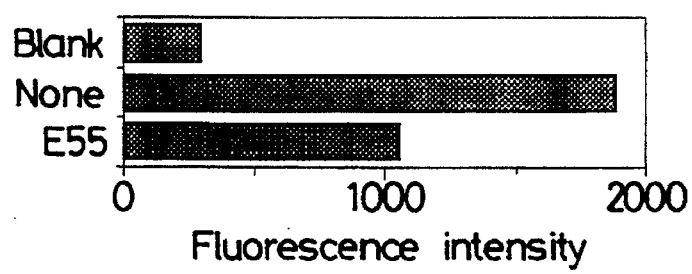
Figure 1:
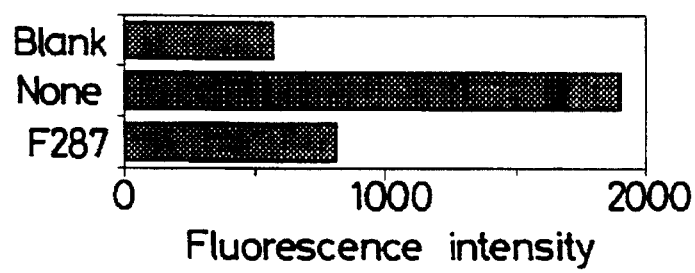
Figure 1:
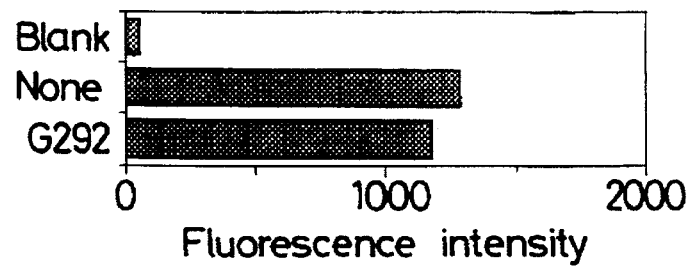

A peptide useful as an antigen to produce an antibody with inhibitory activity of cell adhesion according to the present invention can be obtained, for example, by cutting out, from a CEA expression vector, a base sequence encoding the peptide sequence of domain N and a base sequence encoding the peptide sequence of a part of or the whole part of domain III, joining them together, inserting the thus-joined base sequences in a suitable vector and then expressing them in appropriate cells.

Described specifically, a CEA expression vector is first digested with a suitable restriction enzyme to eliminate DNA fragments encoding domains I and II of CEA. As an alternative, the CEA expression vector is digested by a suitable restriction enzyme to divide it into genes encoding the respective domains and a DNA fragment encoding domain N and another DNA fragment encoding a part of or the entire part of domain III are joined together with ligase.

By a method known per se in the art, the gene so obtained is next inserted in a plasmid which can be expressed in host cells. Host cells (*Escherichia coli*, yeast or animal cells) are transformed, followed by culture.

Since the peptide sequences of domains N and (or domains 3A and 3B) of CEA are both known, it is also possible to produce a peptide according to the present invention or a peptide having homology therewith by a synthetic process instead of the above processes.

To produce the monoclonal antibody of this invention by using the resulting peptide having cell adhesion activity (which may hereinafter be called an "antigen peptide"), a mammal is immunized with the antigen peptide by a method known per se in the art and the spleen is excised to obtain spleen cells. These spleen cells are then fused with subcultured cells. The cells so fused are subjected to screening in an appropriate manner to isolate fused cells in which the target antibody has been expressed. It is then necessary to culture the thus-isolated fused cells in an adequate culture medium.

The above screening can be conducted, for example, by conducting selective culture on HAT culture and, with respect to the culture supernatant, confirming a reaction with the antigen by EIA. If necessary, it is possible to combine a further step in which the culture supernatant is reacted with domain III deletion antigen.

Confirmation as to whether the resulting monoclonal antibody inhibits cell adhesion or not can be achieved, for example, by such a model experiment as will be described next. Namely, a plasmid capable of expressing CEA in animal cells is produced in a manner known per se in the art. The plasmid is then introduced in CHO (Chinese hamster ovary) cells to establish a cell line which can express a CEA antigen on cell surfaces. Next, in the presence of the monoclonal antibody, the cell adhesion activity of the CEA expressing cell line is investigated. The results of the investigation are then compared with the results of an experiment conducted in the absence of the monoclonal antibody.

The cell adhesion activity can be measured by any known appropriate method. For example, a cell line is allowed to grow in a tide tide 24-well plate in advance. Another cell line labeled with a fluorescent substance or radiation is then added to each well and, subsequent to incubation for a predetermined time, each well is washed several times with a buffer to eliminate unadhered cells. Then, the adhered cells are separated, for example, with trypsin or are dissolved with a surfactant such as 1% NP-40. By an appropriate measuring instrument, the intensity of fluorescence or radiation of the adhered cells is measured.

The monoclonal antibody of this invention available as described above can inhibit the cell adhesion activity of CEA, said cell adhesion activity being considered to take part in the metastasis of colon cancer, and a pharmaceutical preparation containing the monoclonal antibody can be used as a cell adhesion inhibitor, for example, a cancer metastasis inhibitor.

It is also possible to produce a mouse-human chimeric antibody and a humanized antibody from the mouse monoclonal antibody of this invention by known techniques [see Nature 312, 643–646 (1984) and Nature 332, 323–327 (1988)]. Use of these antibodies are expected to solve the problem of antigenicity due to continued administration, the problem of in vivo half-life, etc. Such mouse-human chimeric antibody and humanized antibody are obviously included in the present invention.

Described specifically, production of the chimeric antibody requires joining of the variable region of H and L chains of a mouse, said chains having cell adhesion inhibiting activity, with the constant region of human being, followed by the insertion into an adequate expression vector. The chimeric antibody can then be mass-produced in animal cells.

To produce the humanized antibody, on the other hand, only hypervariable regions (CDR1, CDR2 and CDR3), antigen binding sites, out of the variable region of H and L chains of a mouse are transplanted to human antibodies, followed by further treatment as in the case of the chimetic antibody. Mass production therefore becomes feasible likewise.

Production of the cell adhesion inhibitor according to the present invention can be conducted by formulating the monoclonal antibody in an amount as needed into a dosable preparation in a manner known per se in the art.

As an administration route for the cell adhesion inhibitor, parenteral administration using an injection, drip infusion additive, suppository or the like is preferred. In some instances, however, it is also possible to adopt oral administration which makes use of tablets, powder, granules, capsules, syrup or the like. Upon formation of each dosable preparation, a known liquid or solid, diluent or carrier can be used. To formulate an injection, for example, it is only necessary to dissolve the antibody of this invention in injection-grade physiological saline and then adding a conventional salt and excipient, for example, sodium chloride, mannitol, aminoacetic acid and the like so that the resulting solution becomes isotonic with the physiological osmotic pressure.

More specific dosable preparations include, for example, an injection which has been obtained by dissolving 20 mg of the antibody of this invention in 1 ml of injection-grade distilled water and then making the resulting solution isotonic with the salts described above.

No particular limitation is imposed on the amount of the monoclonal antibody according to this invention to be used in the cell adhesion inhibitor. As the antibody has low toxicity and high safety, it is generally sufficient to use the monoclonal antibody in an amount of 1–1,000 mg in the case of parenteral administration.

The present invention will hereinafter be described in further detail by the following Referential Examples and Examples.

Referential Example 1

Preparation of N-III expression vector and development of antigen (CEA N-III)

A CEA deletion antigen N-III expression vector was prepared as will be described next.

Fragments of 6122 bp and 2293 bp, which had been obtained by digesting a CEA expression vector pdKCR-dhfr-CEA [Oikawa, S. et al., B.B.R.C., 164, 39 (1989)] with PstI (product of TAKARA SHUZO CO., LTD.), were joined together with T4DNA ligase, whereby an N-III expression vector pdKCR-dhfr-CEA N-III was prepared.

Introduction of the expression vector into cells and establishment of expression cells were conducted by methods known per se in the art [Oikawa, S. et al., B.B.R.C., 164, 39 (1989)], so that CEA N-III was obtained as an antigen.

The antigen contained, as domain N, a sequence consisting of the 1st to 108th amino acids of CEA and, as domain III, a sequence consisting of the 465th to 642th amino acids of CEA.

Referential Example 2

Preparation of soluble CEA N-III fraction

CHO cells in which pdKCR-dhfr-CEA N-III had been introduced were subjected to PI-PLC treatment as described below, whereby CEA N-III was obtained as an antigen.
(PI-PLC Treatment)

$1.75 \times 10^8$ CHO N-III cells were treated with PBS containing 0.125% of trypsin and 0.01% of EDTA and suspended. Those cells were suspended in 5 ml of PBS, followed by the addition of PI-PLC (product of Funakoshi, Inc., Tokyo) to a final concentration of 0.2 unit/ml. They were reacted at 37° C. for 2 hours.

EXAMPLE 1

Preparation of hybridoma

Preparation of a hybridoma was conducted following the technique proposed by Milstein in Nature, 256, 495 (1975). CHO N-III cells with a CEA N-III expression vector introduced therein or a soluble N-III fraction prepared from the cells was suspended in the Freund's complete adjuvant. The suspension was injected three times at intervals of 7–10 days into the abdominal cavity of a (BALB/c) mouse. Three days after the last immunization, the spleen of the mouse was taken out. Its cells (spleen cells) and mouse myeloma cells were caused to fuse by using polyethylene glycol. Selective culture of fused cells (hybridoma) was then conducted on HAT culture medium (which had been obtained by adding hypoxanthin, aminopterin and thymidine to 10% serum-added RPMI 1640 medium) by a method known per se in the art. Primary screening was thereafter conducted with respect to the culture supernatant by ELISA in view of the reaction to purified CEA.

The hybridoma which had been judged positive by the primary screening was subjected further to subcloning by the limiting dilution analysis so that a monoclonal was obtained. The sub-class of an antibody (MoAb) produced by the monoclonal was determined using a commercial mouse globulin identification kit.

In the manner described above, there were obtained seven hybridoma clones capable of producing an antibody having cell adhesion inhibiting activity, namely, hybridoma clones C249, E55, F287, F361, G125, G213 and G292. Incidentally, hybridomas and monoclonal antibodies produced by the hybridomas will be designated by the same symbols in the present specification.

Of the seven hybridoma clones, hybridoma G125 which produces the representative antibody was deposited Feb. 14, 1992 under FERM BP-3750 with Fermentation Research Institute, Agency of Industrial Science and Technology, Ministry of International Trade and Industry, 1–3, Higashi 1-chome, Tsukuba-shi, Ibaraki-ken 305, Japan.

EXAMPLE 2

Production of monoclonal antibody

The hybridomas obtained in Example 1 were inoculated to the abdominal cavity of a BALB/c mouse, and ascitic fluid was recovered. The thus-obtained ascitic fluid (20 ml) was centrifuged and clarified and was then caused to pass through a 35-ml protein A-Sepharose CL4B column (product of Pharmacia LKB AB). After the column was washed with a 1.5M glycine buffer (pH 8.9) which contained 3M of sodium chloride, the monoclonal antibody adsorbed on the column was eluted with 0.1M citric acid buffer (pH 4.0).

Seven kinds of monoclonal antibodies C249, E55, F165, F287, F361, G125, G213 and G292 obtained as described above were found to belong to immunoglobulin sub-classes shown in the following Table.

TABLE 1

| Group* | Clone | Class |
|---|---|---|
| 1 | C249 | IgG1 (κ) |
|  | E55 | IgG2a (κ) |
|  | F287 | IgG1 (κ) |
| 2 | G125 | IgG1 (κ) |
| 3 | F361 | IgG1 (κ) |
|  | G213 | IgG1 (κ) |
|  | G292 | IgG1 (κ) |

*The groups are divided by epitopes recognized by the antibody. Namely, group 1 recognizes domain N (CEA specific), group 2 domain N (common with NCA), and group 3 domain III, all as epitopes.

EXAMPLE 3

Preparation of Fab fraction

Each monoclonal antibody obtained in Example 2 was incubated at 22° C. for 8 hours together with papain-bound beads (commercial product) so that it was cut. After the supernatant was collected, it was passed through a protein A-Sepharose CL4B column and a through fraction was obtained as an Fab fraction.

EXAMPLE 4

Measurement of cell adhesion inhibiting activity

Measurement of cell adhesion inhibiting activity was conducted by a conventional technique, that is, following the cell adhesion assay described by Oikawa, S. et al. in B.B.R.C., 164, 39 (1989). Namely, the CHO cell line (CHO/CEA) capable of expressing $1 \times 10^7$ of CEA was fluorescein-labelled with PKH2 (product of Xynaticis Company) and then suspended in 3 ml of a culture medium. 0.1 ml of the suspension was added to the non-labelled CHO/CEA cell line which had grown as a monolayer in each well of a 24-well plate, followed by incubation at 37° C. for 30 minutes in a 5% $CO_2$ incubator. After each well was washed twice with PBS, adhered cells were separated by 0.1% trypsin and the fluorescence intensity was measured by a fluorescence intensity meter. Adhesion of the labelled CHO/CEA cells to CEA non-expressing CHO cells was used as a blank.

EXAMPLE 5

Inhibition of CEA-mediated cell adhesion by monoclonal antibody

Using the Fab fraction prepared from each antibody, the cell adhesion assay was conducted at 37° C. for 30 minutes. Namely, it was investigated in the presence of 27 μg/ml of the Fab fraction how much the homotypic adhesion activity of CEA would be inhibited. Incidentally, "None" indicates cell adhesion activity in the absence of an antibody. The results are shown in FIG. 1. From FIG. 1, the percent adhesion inhibition was calculated in accordance with the following formula:

$$\text{Adhesion inhibition, \%} = \frac{A_2 - A_1}{A_2 - B} \times 100$$

Figure 2:
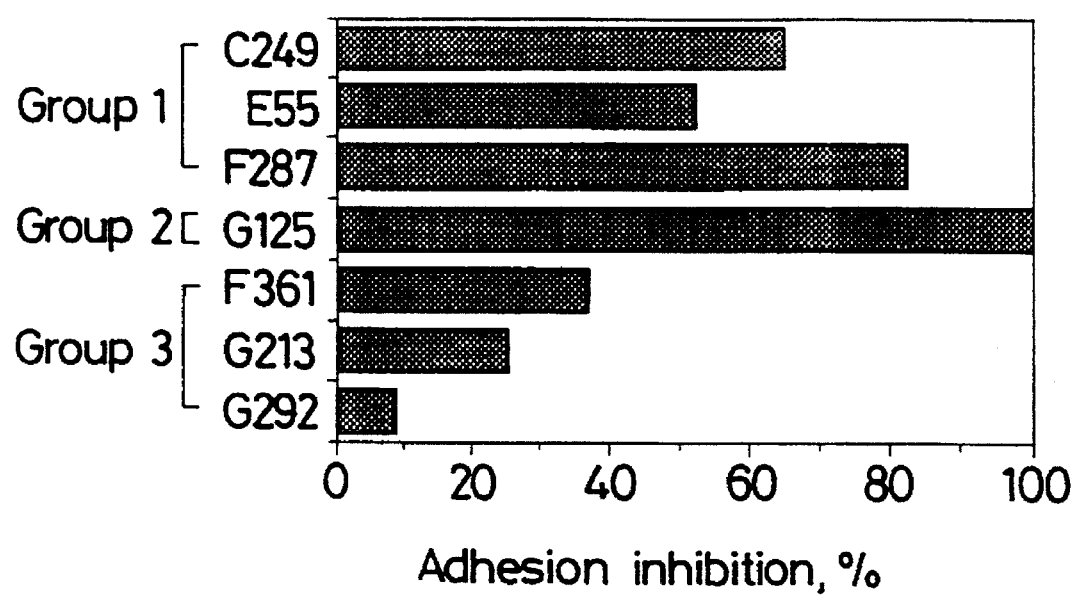
FIG. 2 diagrammatically depicts percent adhesion inhibitions by monoclonal antibodies of the present invention against CEA.

$A_1$: Homotypic adhesion activity of CEA in the presence of Fab fraction $A_2$: Homotypic adhesion activity of CEA in the absence of Fab fraction B: Adhesion activity of blank One example of the above results is diagrammatically illustrated in FIG. 2. As is seen from the results of FIG. 2, an epitope-dependent difference was observed with respect to the adhesion inhibiting activity of each antibody (Fab fraction). Namely, the domain-N-recognizing antibody exhibited relatively high inhibiting activity compared with the domain-III-recognizing antibody. In particular, G125 (Group 2) had strong activity of 100%. Further, C249, E55 and F287 (Group 1) showed intermediate inhibition of from 51.8% to 82.1%.

EXAMPLE 6

Inhibition to liver metastasis by monoclonal antibody

In the presence of 50 μg of each monoclonal antibody (Fab fraction), $2 \times 10^6$ of CHO/CEA cells were incubated at 4° C. for 1 hour. A nude mouse was incised into the abdominal cavity under anesthesia and the cell suspension obtained as described above was introduced into the spleen. Seventeen days later, the weight of the liver as well as the presence or absence of any metastasized lesion(s) and the number of metastasized nodule(s) in the liver were determined as indices of the extent of metastasis. The results are presented in Table 2 as the liver weight, incidence of metastasized mice and the metastasized nodule(s) number, respectively.

TABLE 2

| Antibody[1] | Amount used (μg/mouse) | Liver weight (g) | Incidence of metastasized mice (# of mice) (%) | Metastasized nodule(s) number (nodule(s)/mouse) |
|---|---|---|---|---|
| C249 | 50 | 1.82 ± 0.13* | 5/8 [62.5] | 23, 5, 3, 3, 2, 0, 0, 0 |
| G125 | 50 | 1.67 ± 0.16** | 4/7 [57.1] | 12, 6, 5, 2, 0, 0, 0 |
| Normal mouse IgG (comparison) | 50 | 3.48 ± 1.76 | 7/8 [87.5] | >50, >50, >50, >50, >50, >50, 2, 0 |
| None (control) | — | 2.34 ± 0.54 | 8/8 [100] | >50, >50, 45, 38, 35, 28, 4, 3 |

[1] As each antibody, its Fab fraction was used.
*P < 0.05 relative to an untreated group as calculated by the Student's t-test.
** P < 0.01 relative to an untreated group as calculated by the Student's t-test.

As is evident from Table 2, the metastasis of CHO/CEA cells to the liver was inhibited by the C249 or G125 pre-treatment. As a comparison, an Fab fraction prepared from an IgG fraction of a normal mouse was employed. As is shown in Table 2, no metastatic inhibition was observed at all in this comparative group. These results indicate that a monoclonal antibody capable of inhibiting the cell adhesion activity of CEA is useful as a cancer metastasis inhibitor.

Industrial applicability

It has heretofore been unable to effectively prevent metastasis of a cancer to other organs. Administration of a monoclonal antibody according to the present invention, however, can inhibit the adhesion activity of cancer cells and, as a result, can prevent metastasis of cancer cells to other organs. The monoclonal antibody is therefore effective as a cell adhesion inhibitor, for example, cancer metastasis inhibitor.

We claim:

1. A method for inhibiting the metastasis of colon cancer to the liver in a living body, which comprises:

administering, in advance of cell metastasis, a monoclonal antibody which specifically binds a peptide which comprises at least the peptide sequence of domain N in the glycoprotein of human carcinoembryonic antigen.

2. The method of claim 1, wherein the cells which express the glycoprotein of human carcinoembryonic antigen on the cell surfaces thereof are colon cancer cells.

3. The method of claim 1, wherein said monoclonal antibody is FERM BP-3750.

4. The method as claimed in claim 1, wherein cell adhesion activity is inhibited by an antibody which binds domain N of human carcinoembryonic antigen.

* * * * *

UNITED STATES PATENT AND TRADEMARK OFFICE
CERTIFICATE OF CORRECTION

PATENT NO. : 5,648,078
DATED : July 15, 1997
INVENTOR(S) : Junko HASHINO, et al.

It is certified that error appears in the above-indentified patent and that said Letters Patent is hereby corrected as shown below:

On the title page, Item [87] should read:

--PCT Pub. No.: WO93/16193

PCT Pub. Date: Aug. 19, 1993--

Signed and Sealed this

Seventh Day of October, 1997

Attest:

BRUCE LEHMAN

*Attesting Officer*          Commissioner of Patents and Trademarks